(12) United States Patent
Neelakanta et al.

(10) Patent No.: US 9,687,151 B2
(45) Date of Patent: Jun. 27, 2017

(54) DEVICE WITH SIMULTANEOUS X-RAY AND INFRARED IMAGE ACQUISITION AND PROCESSING SYSTEM FOR ENHANCED BREAST IMAGING

(71) Applicant: TUSCANO EQUIPMENTS PRIVATE LIMITED, Chennai (IN)

(72) Inventors: Kannan Neelakanta, Chennai (IN); Jayanthi Anand, Chennai (IN); Sudhan Chandrasekaran, Coimbatore (IN); Rajendran Cherukandath, Coimbatore (IN); Jayaraman Kiruthi Vasan, Chennai (IN)

(73) Assignee: TUSCANO EQUIPMENTS PRIVATE LIMITED, Chennai (IN)

( * ) Notice: Subject to any disclaimer, the term of this patent is extended or adjusted under 35 U.S.C. 154(b) by 412 days.

(21) Appl. No.: 14/361,315

(22) PCT Filed: Nov. 29, 2012

(86) PCT No.: PCT/IN2012/000778
§ 371 (c)(1),
(2) Date: May 29, 2014

(87) PCT Pub. No.: WO2013/080223
PCT Pub. Date: Jun. 6, 2013

(65) Prior Publication Data
US 2014/0336502 A1    Nov. 13, 2014

(30) Foreign Application Priority Data

Dec. 1, 2011 (IN) .......................... 4165/CHE/2011

(51) Int. Cl.
*A61B 6/00* (2006.01)
*A61B 5/00* (2006.01)
(Continued)

(52) U.S. Cl.
CPC .......... *A61B 5/0035* (2013.01); *A61B 5/0091* (2013.01); *A61B 5/708* (2013.01);
(Continued)

(58) Field of Classification Search
None
See application file for complete search history.

(56) References Cited

U.S. PATENT DOCUMENTS 4,407,292 A * 10/1983 Edrich .................. A61B 5/015
374/122
6,144,875 A * 11/2000 Schweikard ........... A61B 19/20
378/69
(Continued)

*Primary Examiner* — Tse Chen
*Assistant Examiner* — Joanne Hoffman
(74) *Attorney, Agent, or Firm* — Barry Choobin; Patent 360 LLC

(57) ABSTRACT

The embodiments herein discloses a device with simultaneous X-ray and infrared acquisition and processing systems for an enhance breast imaging. The device has a positioning assembly housed inside a closed chamber and provided with the Infrared and X-ray imaging systems to simultaneously capture an infra red image and an X-ray image of the breast under examination. A patient support table with an opening is provided to enable a patient to lie in a prone position without compressing a breast during imaging. The device is used to correlate anatomical and physiological characteristics and post process analysis of a breast tissue thereby reducing a number of to false positive results. Further the device helps in focusing on a suspected area in a follow-up procedure and aids post processing treatment like targeted biopsy and targeted radiation.

15 Claims, 4 Drawing Sheets

(51) Int. Cl.
*A61B 6/03* (2006.01)
*A61B 6/04* (2006.01)
*A61B 6/12* (2006.01)
*A61B 10/02* (2006.01)

(52) U.S. Cl.
CPC ............ *A61B 6/032* (2013.01); *A61B 6/0435* (2013.01); *A61B 6/12* (2013.01); *A61B 6/4417* (2013.01); *A61B 6/502* (2013.01); *A61B 6/5247* (2013.01); *A61B 10/02* (2013.01)

(56) References Cited

U.S. PATENT DOCUMENTS

| | | | | |
|---|---|---|---|---|
| 2005/0234327 | A1* | 10/2005 | Saracen | A61B 6/0457 600/407 |
| 2007/0211854 | A1* | 9/2007 | Koshnitsky | A61B 6/0414 378/65 |
| 2008/0221443 | A1* | 9/2008 | Ritchie | A61B 6/548 600/427 |
| 2008/0275310 | A1* | 11/2008 | Kim | A61B 5/015 600/300 |
| 2010/0111250 | A1* | 5/2010 | Tsujii | A61B 5/0091 378/37 |
| 2010/0284591 | A1* | 11/2010 | Arnon | A61B 5/015 382/128 |
| 2011/0015514 | A1* | 1/2011 | Skalli | G06F 19/3437 600/407 |

* cited by examiner

DEVICE WITH SIMULTANEOUS X-RAY AND INFRARED IMAGE ACQUISITION AND PROCESSING SYSTEM FOR ENHANCED BREAST IMAGING

CROSS-REFERENCE TO RELATED APPLICATIONS

The present application is a national phase application to the PCT Application entitled, "A Device with Simultaneous X-Ray and Infrared Image Acquisition and Processing System for Enhanced Breast Imaging" with serial number PCT/IN 2012/000778, filed at Government of India Patent Office on Nov. 29, 2012, the content of which is incorporated by reference herein.

The present application claims the priority of the Indian Patent application No. 4165/CHE/2011 filed on Dec. 1, 2011 with the title, "A Device with Simultaneous X-Ray and Infrared Image Acquisition and Processing System for Enhanced Breast Imaging" and the contents of which are incorporated in entirety by reference herein.

BACKGROUND

Technical Field

The embodiments herein generally relate to the field of imaging devices for medical diagnostics and particularly relates to the imaging devices used for detecting a breast cancer. The embodiments herein more particularly relate to an imaging device with simultaneous digital X-Ray and infrared image acquisition and processing systems in conjunction with a positioning apparatus thereby providing an enhanced solution for imaging a breast.

Description of the Related Art

The breast cancer is the commonest form of cancer in the women in worldwide. It is one of the leading causes of death in most of the countries. Especially in India, it is evident from the various statistics that the breast cancer accounts for about 25% to 33% of all cancers in the women. However, if breast cancer is detected at an early stage, then an average survival rate can be exceeded by five years or more.

A Breast cancer screening refers to a medical screening of an asymptomatic, apparently healthy woman for breast cancer in an attempt to achieve an earlier diagnosis. The assumption is that early detection will improve the outcomes. A number of screening test have been employed and the screening tests include a clinical and self breast exams, a mammography, a genetic screening, an ultrasound imaging and a magnetic resonance imaging processes.

In general, there are multiple methods for early detection of breast cancer using diagnostic imaging equipments. The commonly used method is an X-Ray Mammography. In another method, an ultrasound imaging system is used. In yet another method, an MRI imaging is used and finally the most evolving method is the use of Thermography i.e., thermal imaging of a breast.

Though the X-Ray based mammography is considered as a gold standard tool available today for breast cancer, most of the women feel discomfort during the procedure. Each breast is compressed with the help of a compression paddle and this causes an acute discomfort to the patient since breast is considered two to three times more sensitive in women. Nearly 5%-15% of mammograms require a follow-up testing but a sizeable percentage of patients do not turn up for the follow-up procedures because of the discomfort caused by compression. Besides a discomfort, another drawback of the mammography is the generation of false negative and false positive results due to a compression of three dimensional breast organ images to a two dimensional film or image, thereby leading to different interpretations. The second widely used technique. Ultrasound mammography also has unique advantages but it lacks repeatability & reproducibility as the compression pressure applied by the sonologist during imaging is not tracked and hence it is difficult to reproduce the results.

Secondly it is difficult to position a suspected spot, which is identified in the initial study, in a follow-up procedure. A penetration of the ultrasound waves in a dense breast is also a matter of concern.

The other screening method used presently is a Magnetic resonance imaging (MRI) which has shown to detect cancers not visible on mammograms. However, a breast MRI has long been regarded to have the following disadvantages. For example, although it is sensitive by more than 27-36%, it has been claimed to be less specific than mammography. As a result, the MRI studies may provide more false positives (up to 30%), which may lead to undesirable financial and psychological costs. The MRI based study requires very expensive MRI scanners and also a coil which is specific for positioning a breast. Further, an MRI may not be used for screening the patients with a pacemaker or breast reconstruction patients with a tissue expander due to the presence of metal. As a result very few procedures are performed with the MRI scanners.

The most useful and evolving method, the Thermography, commonly called as an infrared thermal imaging, uses the highly specialized infra red cameras to measure a heat coming from a surface of a breast tissue. The thermal pattern of a patient's breast is collected with a help of the infrared camera in a non contact manner. The human body dissipates the heat through a skin to maintain itself in a thermal equilibrium. The quantity of heat emitted depends on an environment and also an exposure of skin to that environment. The tissues tend to expend more energy when they multiply and they are usually accompanied by an increased blood supply due to a development of new vessels (angiogenesis). The tumor cells, in general, may have an increased blood supply and also a development of the additional vessels (angiogenesis), as well as an increased metabolic rate, which in turn translates into the increased temperature gradients compared to a surrounding normal tissue. Detecting these infrared "hotspots" and gradients can help to identify and diagnose a tissue heat pattern thereby leading to a conclusion regarding a normal or an abnormal growth of tissues in a specific area. A Breast Thermography, when done in a controlled and repeatable manner, has yielded very accurate results, but only in the hands of a trained personnel using the correct type of Thermography cameras. Today's infrared cameras are capable of sensing the changes in temperature at 0.08° C. or better and do not require any contact with a patient. But, in most of the existing Thermography procedures, the images are captured in a patient standing or sitting position with the breast(s) facing the thermal camera (frontal view). A single image or a series of images is taken and they are compared. A fundamental flaw in such an approach is that the rest of the body also dissipates heat and there is a possibility that this can alter or influence the environment regarding a heat pattern. Few Thermography techniques do capture the heat patterns of the breast in a patient lying in a prone position but do not capture all the views of the breast in a direct manner.

All of the above screening techniques provide either a physiological or anatomical view of the breast. Each year, millions of women around the world are subjected to the unnecessary breast biopsies because of inadequacies of cancer detection and inability to separate a benign from the cancerous lesions.

Hence there is strong felt a need to develop a novel and more effective screening device with high sensitivity and repeatability to overcome the aforementioned drawbacks in various screening techniques for breast cancer.

The above mentioned shortcomings, disadvantages and problems are addressed herein and which will be understood by reading and studying the following specification.

OBJECTS OF THE EMBODIMENTS

The primary object of the embodiments herein is to provide an imaging device with a simultaneous digital X-Ray and Infrared red image acquisition and processing systems in conjunction with a positioning apparatus for a minimal radiation.

Another object of the embodiments herein is to develop an imaging device to provide both the anatomical and physiological views of a breast simultaneously for an early detection of the abnormalities.

Still another object of the embodiments herein is to develop an imaging device so that each modality is used independently and/or in a concurrent fashion as needed or desired to provide the images of a suspected area.

Yet another object of the embodiments herein is to develop an imaging device to allow a capturing of time based thermal images of multiple views, including but not limited to cranial, medial, caudal, lateral and frontal views of a breast.

Yet another object of the embodiments herein is to develop an imaging device to enable a focusing on a suspected area in a follow-up procedure and also to assist in a post processing treatment like targeted biopsy as well as a targeted radiation.

These and other objects and advantages of the embodiments herein will become readily apparent from the following detailed description taken in conjunction with the accompanying drawings.

SUMMARY

The various embodiments herein provide a device with simultaneous X-ray and infrared acquisition and processing systems for an enhanced breast imaging to correlate anatomical and physiological characteristics of a breast and for a post processing of a 3D analysis. According to an embodiment herein, the device comprises a positioning assembly and an X-ray imaging system is mounted on the positioning assembly. An infrared imaging system is mounted on the positioning assembly. A closed chamber is provided to house or enclose the positioning assembly. A patient support table is provided to enable a patient to lie in a prone position and an opening is provided on the patient support table for extending a breast of a patient to be examined, through the patient table to acquire an image of the breast to be examined.

According to an embodiment herein, the positioning assembly is mounted with the Infrared imaging system and the X-ray imaging system to capture an infra red image of the breast to be examined and an X-ray image of the breast to be examined simultaneously.

According to an embodiment herein, the X-ray imaging system comprises an X-ray suture to emit an X-ray radiation which passes through the breast to be examined and an X-ray detector for receiving the X-ray radiation which is passed through the breast to be examined to generate an X-ray image of the breast to be examined, and the X-ray detector is placed close to a periphery of the breast to be examined.

According to an embodiment herein, the infrared imaging system has a plurality of infrared cameras to acquire a plurality of infrared images of the breast to be examined, on a time basis. The plurality of infrared cameras includes a first infrared camera which is arranged in parallel to the X-ray source, a second infrared camera which is arranged in perpendicular to the X-ray source. The plurality of infrared images includes a cranial image, a medial image, a candid image, a lateral image and a frontal image.

According to an embodiment herein the first infrared camera focus a portion of the breast under an X-ray radiation and captures the cranial image, the medial image, the caudal image, the lateral image and the frontal image of the breast and wherein the second infrared camera captures the other portions of the breast at multiple views. The multiple views include the cranial image, the medial image, the caudal image, and the lateral image of the breast According to an embodiment herein, the positioning assembly has a microcontroller to move the X-ray source and the plurality of infrared cameras along an x-axis and a y-axis, to rotate the X-ray source, an X-ray detector and the plurality of infrared cameras, and to tilt a camera axis of the plurality of infrared cameras based on a command provided by a user through a personal computer. The microcontroller is communicatively connected to the personal computer.

According to an embodiment herein, the microcontroller actuates a respective motor to move the X-ray source and the plurality of infrared cameras along the x-axis, the y-axis, a rotational axis and to tilt the camera axis of the plurality of infrared cameras.

According to an embodiment herein, the positioning assembly positrons the infrared imaging system and the X-ray imaging system at a same coordinate point to acquire an image of both a right breast and a left breast of a patient for comparison.

According to an embodiment herein, the Infrared imaging system and the X-ray imaging system are rotated simultaneously around a vertical axis in relative to the opening to acquire a full 360 degree view of the breast to be examined.

According to an embodiment herein, the microcontroller positions the Infrared imaging system and the X-ray imaging system to detect any abnormalities suspected. The microcontroller positions the X-ray source to expose a suspected spot to a targeted radiation for a post process treatment. The microcontroller positions a biopsy device to the suspected spot for a targeted biopsy procedure.

According to an embodiment herein the Infrared imaging system and the X-ray imaging system are moved along a horizontal axis towards or away from the breast to be examined to perform an enhanced analysis.

According to an embodiment herein, the Infrared imaging system and the X-ray imaging system are not allowed to be positioned within 20 cm from the edge of the opening in case of an imaging of side views and wherein the infrared imaging system and the X-ray imaging system are not allowed to be positioned within 20 cm from the center of the opening in case of a frontal imaging at any instant so that no portion of the Infrared imaging system and the X-ray imaging system come into contact or touch the breast to be examined.

According to an embodiment herein, the microcontroller rotates the plurality of infrared cameras to any required degree to screen a complete portion of the breast to be examined.

According to an embodiment herein, a radiation impact of the X-Ray imaging system on a tissue of the breast is studied with the infrared images acquired from the Infrared imaging system.

According to an embodiment herein, the infrared imaging system and the X-ray imaging system are used independently or simultaneously to cover a full portion of the breast for acquiring a desired image.

According to an embodiment herein, the infrared imaging system and the X-ray imaging system are designed in such a way that a positioning of the infrared imaging system does not interfere with an operating position of the X-ray imaging system.

According to an embodiment herein, the patient support table is configured to support the patient and exposes only the breast for screening and without making any discomfort to the patient.

According to an embodiment herein, the patient support table and the closed chamber are coated with Lead (Pb) to avoid a leakage of an X-Ray radiation.

According to an embodiment herein, a temperature and a humidity of the closed chamber is controlled and set as desired by a user.

According to an embodiment herein, the X-Ray source is mounted near the plurality of infrared cameras or at 90 degrees in a same plane so that is same portion of the breast is screened simultaneously by the X-ray imaging system and by the infrared imaging system to overlap a physiological characteristics of the breast with an anatomical characteristics of the breast to provide an enhanced analysis.

The embodiments herein provide an imaging device with an integrated system for a simultaneous acquisition and processing of digital X-Ray and Infra Red images for an enhanced breast imaging process. The device comprises a patient support table with a positioning assembly mounted with an X-ray system and an Infra red imaging system. The entire positioning assembly is placed in a closed chamber with a controlled temperature and humidity conditions.

The positioning assembly comprises a microcontroller which positions the four axes, such as an X-axis, a Y-axis, a rotational axis and a camera axis, based on the commands received from a user interface provided in a processing system like personal computer. Each axis is actuated by a separate motor which is driven by the microcontroller. By actuating the X-axis, the Infrared imaging system and X-Ray imaging system are moved along a horizontal axis. The IR camera which is parallel to the X-ray source usually moves along the horizontal axis along with Y axis and camera axis to capture a frontal shot of the breast. Similarly, by actuating the Y-axis along with rotational axis and camera axis, both the modalities are positioned to image the side views like caudal, cranial, medial and lateral portion of the breast and also allow the system to capture a 360 degree view of the breast. The Camera axis is actuated to provide any desired tilt to the IR camera to capture the breast thermal image.

The device of the embodiments herein provides both an anatomical and a physiological view of the breast simultaneously for an early detection of the abnormalities. In addition to the above, each modality is used independently and/or in a concurrent fashion as needed or desired. The images from both the modalities are overlapped to correlate the anatomical and physiological views of the suspected area.

Further, in the embodiments herein, the diagnosis is performed based on an outcome of the two modalities taken simultaneously, thereby leading to a reduction in a number of false positive results when compared to the conventional techniques.

Moreover it increases a screening of a follow up process as there is no pain or compression or any discomfort to the patients during the scan/procedure.

These and other aspects of the embodiments herein will be better appreciated and understood when considered in conjunction with the following description and the accompanying drawings. It should be understood, however, that the following descriptions, while indicating the preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
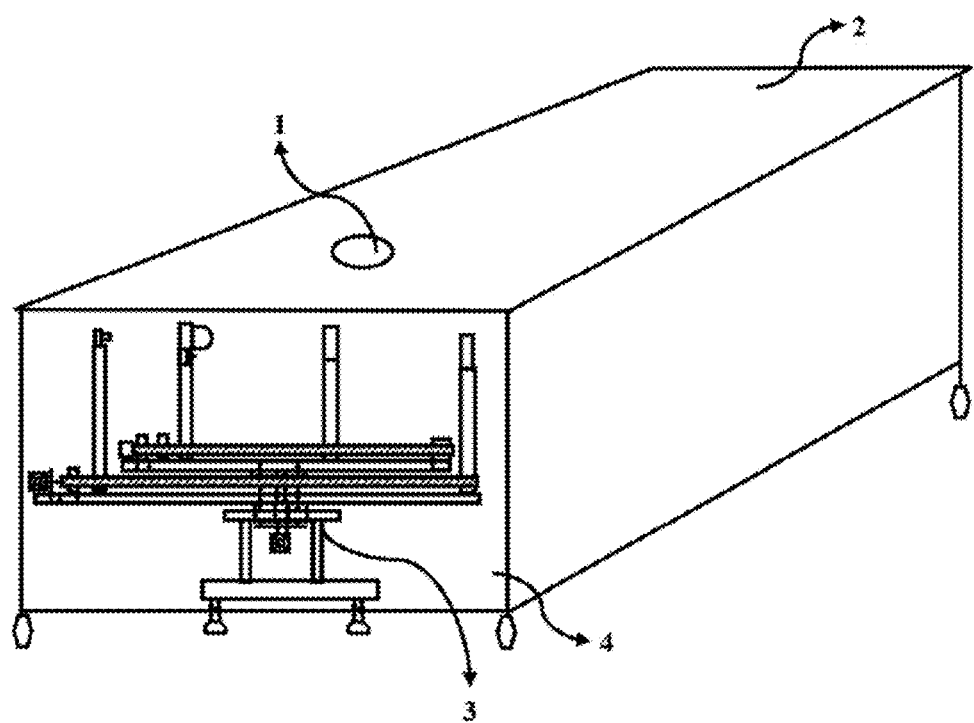
FIG. 1 illustrates a front perspective view of an imaging device with a simultaneous digital X-Ray and infrared image acquisition and processing systems, according to an embodiment herein.

Although the specific features of the embodiments herein are shown in some drawings and not in others. This is done for convenience only as each feature may be combined with any or all of the other features in accordance with the embodiment herein.

DETAILED DESCRIPTION OF THE EMBODIMENTS HEREIN

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a device with simultaneous X-ray and infrared acquisition and processing systems for an enhanced breast imaging to correlate anatomical and physiological characteristics of a breast and for a post processing of a 3D analysis. According to an embodiment herein, the device comprises a positioning assembly and an X-ray imaging system is mounted on the positioning assembly. An infrared imaging system is mounted on the positioning assembly. A closed chamber is provided to house or enclose the positioning assembly. A patient support table is provided to enable a patient to lie in a prone position and an opening is provided on the patient support table for extending a breast of a patient to be examined, through the patient table to acquire an image of the breast to be examined.

According to an embodiment herein, the positioning assembly is mounted with the Infrared imaging system and the X-ray imaging system to capture an infra red image of the breast to be examined and an X-ray image of the breast to be examined simultaneously.

According to an embodiment herein, the X-ray imaging system comprises an X-ray source to emit an X-ray radiation which passes through the breast to be examined and an X-ray detector for receiving the X-ray radiation which is passed through the breast to be examined to generate an X-ray image of the breast to be examined, and the X-ray detector is placed close to a periphery of the breast to be examined.

According to an embodiment herein, the infrared imaging system has a plurality of infrared cameras to acquire a plurality of infrared images of the breast to be examined, on a time basis. The plurality of infrared cameras includes a first infrared camera which is arranged in parallel to the X-ray source, a second infrared camera which is arranged in perpendicular to the X-ray source. The plurality of infrared images includes a cranial image, a medial image, a caudal image, a lateral image and a frontal image.

According to an embodiment herein, the first infrared camera focuses a portion of the breast under an X-ray radiation and the second infrared camera captures the cranial image, the medial image, the caudal image and the lateral image of the breast.

According to an embodiment herein, the positioning assembly has a microcontroller to move the X-ray source and the plurality of infrared cameras along an x-axis and a y-axis, to rotate the X-ray source and the plurality of infrared cameras, and to tilt a camera axis of the plurality of infrared cameras based on a command provided by a user through a personal computer. The microcontroller is communicatively connected to the personal computer.

According to an embodiment herein, the microcontroller actuates a respective motor to move the X-ray source and the plurality of infrared cameras along the x-axis, the y-axis, a rotational axis and to tilt the camera axis of the plurality of infrared cameras.

According to an embodiment herein, the positioning assembly positions the infrared imaging system and the X-ray imaging system at same coordinate point to acquire an image of both a right breast and a left breast of a patient for comparison.

According to an embodiment herein, the Infrared imaging system and the X-ray imaging system are rotated simultaneously but at different coordinates on requirement around a vertical axis in relative to the opening to acquire a full 360 degree view of the breast to be examined.

According to an embodiment herein, the microcontroller positions the Infrared imaging system and the X-ray imaging system to detect any abnormalities suspected. The microcontroller positions the X-ray source to expose a suspected spot to a targeted radiation for a post process treatment. The microcontroller positions a biopsy device to the suspected spot for a targeted biopsy procedure.

According to an embodiment herein, the Infrared imaging system and the X-ray imaging system are moved along a horizontal axis towards or away from the breast to be examined to perform an enhanced analysis.

According to an embodiment herein, the Infrared imaging system and the X-ray imaging system are not allowed to be positioned within 20 cm from the edge of the opening in case of a side view imaging and from the center of the opening in case of a frontal imaging at any instant so that no portion of the Infrared imaging system and the X-ray imaging system come into contact or touch the breast to be examined.

According to an embodiment herein, the microcontroller tilts the plurality of infrared cameras to any required degree to screen a complete portion of the breast to be examined.

According to an embodiment herein, a radiation impact of the X-Ray imaging system on a tissue of the breast is studied with the infrared images acquired from the Infrared imaging system. The IR imaging system is also used to image the breast tissue for screening and diagnostic purposes.

According to an embodiment herein, the infrared imaging system and the X-ray imaging system are used independently or simultaneously to cover a full is portion of the breast for acquiring a desired image.

According to an embodiment herein, the infrared imaging system and the X-ray imaging system are designed in such a way that a positioning of the infrared imaging system does not interfere with an operating position of the X-ray imaging system.

According to an embodiment herein, the patient support table is configured to support the patient and exposes only the breast for screening and without making any discomfort to the patient.

According to an embodiment herein, the patient support table and the closed chamber are coated with Lead (Pb) to avoid a leakage of an X-Ray radiation.

According to an embodiment herein, a temperature and a humidity of the closed chamber is controlled and set as desired by a user.

According to an embodiment herein, the X-Ray source is mounted near the plurality of infrared cameras or at 90 degrees in a same plane so that a same portion of the breast is screened simultaneously by the X-ray imaging system and by the infrared imaging system to overlap a physiological characteristics of the breast with an anatomical characteristics of the breast to provide an enhanced analysis.

FIG. 1 illustrates a front perspective view of an imaging device with a simultaneous digital X-Ray and Infrared red image acquisition and processing systems, according to an embodiment herein. With respect to FIG. 1, the device comprises of patient support table 2, preferably an examination table and wherein the patient lies in a prone position such that a breast of a patient to be imaged is extended through a hole, such as an opening 1 in the patient support table 2. The breast of the patient is preferably extended downward through the opening 1. A closed chamber 4 is arranged below the patient support table. The bottom surface of the patient examination table as well as closed chamber is coated with X-ray radiation absorbing material like Lead (Pb) to avoid radiation leakage outside the chamber. A positioning assembly 3 is provided inside the closed chamber. An X-ray imaging system is mounted on the positioning assembly 3 and an infrared imaging system is mounted on the positioning assembly 3 to capture an X-ray image of the breast to be examined and an infra red image of the breast to be examined simultaneously.

The commercially available infrared cameras are mounted on the positioning assembly 3. The entire positioning assembly is placed in a closed chamber 4 and a temperature and a humidity of an environment inside the closed chamber 4 is controlled.

The positioning assembly comprises a microcontroller which will position to control the four axes such as the X, Y, Rotational and camera axes based on the commands from PC. Each axis is actuated by a separate motor which is driven by the microcontroller. By actuating the X-Axis, the IR cameras and X-Ray source are moved along a horizontal axis. The IR camera which is arranged in parallel to the X-ray source usually moves along the horizontal axis to capture a frontal shot of the breast. Similarly, by actuating the Y-Axis, both the modalities are positioned to image the side views of the breast, for example, the caudal, cranial, medial and lateral portion of the breast. Also by actuating, the Y-axis and camera axis, the frontal view is imaged. Finally by actuating rotational axis, the system allowed to capture a full 360 degree view of the breast. The camera axis is actuated/tilted to provide any desired tilt to the IR camera to capture the breast thermal image.

Figure 2:
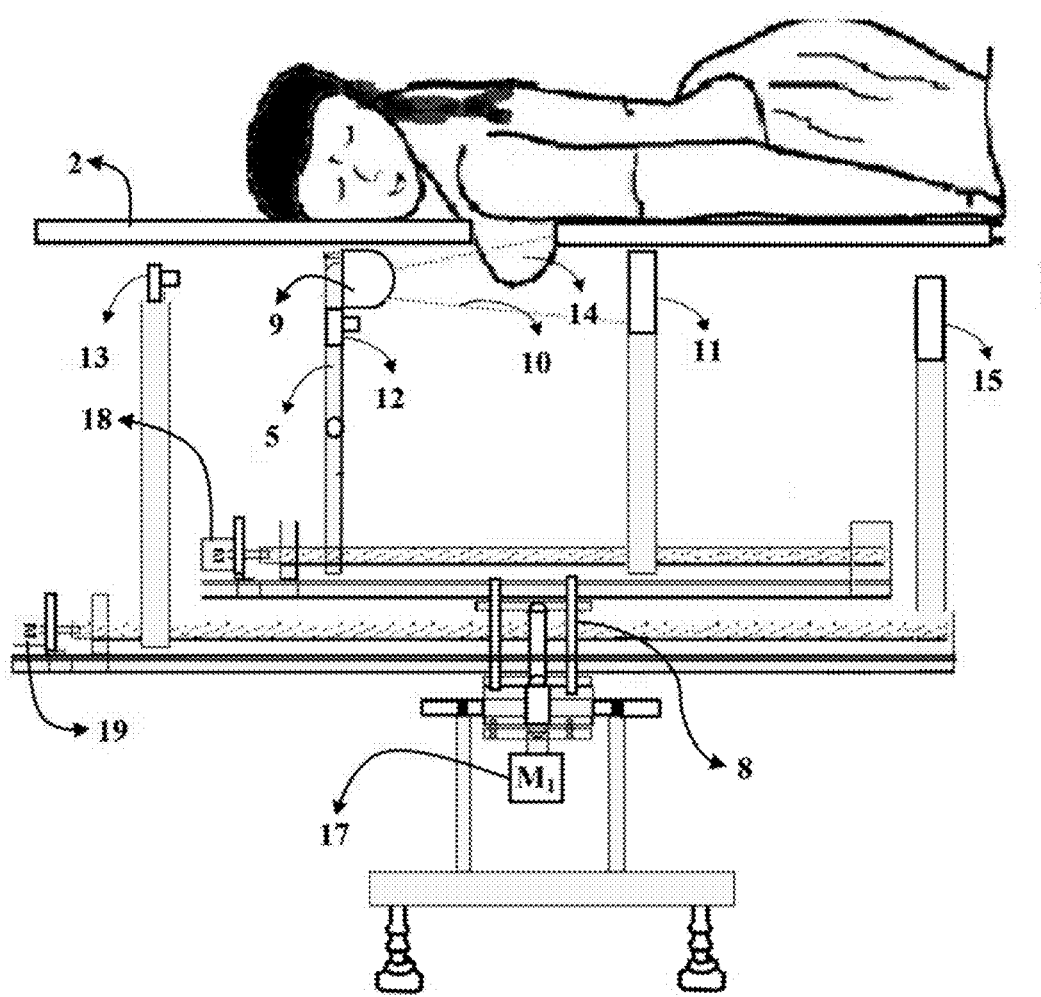
FIG. 2 illustrates a side view of a positioning assembly mounted with the X-Ray imaging system in an imaging device with a simultaneous digital X-Ray and Infrared red image acquisition and processing systems, and the positioning/biopsy facilitating system according to an embodiment herein.

FIG. 2 illustrates a side view of a positioning assembly mounted with the X-Ray imaging system in an imaging device with a simultaneous digital X-Ray and Infrared red image acquisition and processing systems, according to an embodiment herein.

With respect to FIG. 2, the X-ray system comprises an X-Ray source 9 which is usually mounted near the infrared camera 12 or at 90 degrees in the same plane so that same portion of the breast 14 is screened simultaneously by the X-ray 10 as well as Thermography and the physiological and anatomical character of the breast 14 are overlapped to provide an enhanced analysis. The patient is made to lie on a patient support table 2 provided with an opening so that the breast is extended through the opening.

This X-Ray source 9 within the temperature controlled chamber provides a steam of x-ray radiation 10 such that the x-rays 10 pass through the patient's breast 14 and are received by an opposing x-ray detector 11 configured to receive the same. The X-ray detector 11 is placed very close to the periphery of the breast 14.

Ideally, the positioning assembly has a common support system to support both the infrared cameras 12, 13 as well as the X-ray imaging system. The commercially available infrared cameras 12, 13 are mounted on the positioning assembly. The entire positioning assembly is placed in a closed chamber and a temperature and a humidity of an environment inside the closed chamber is controlled.

The positioning assembly comprises a microcontroller which will position to control the four axes such as the X-axis, Y-axis, Rotational axis 8 and camera axis 5 based on the commands from PC. Each axis is actuated by a separate motor 17, 18, 19 which is driven by the microcontroller. By actuating the X-Axis, the IR cameras 12, 13 mounted on two different arms and the X-Ray source 9 are moved along a horizontal axis. The IR camera 12 which is arranged in parallel to the X-ray source 9 usually moves along the horizontal axis and the vertical axis to capture a frontal shot of the breast 14. The movement is limited by X-axis motor to avoid injury to the tissue being imaged. Similarly, by actuating the two IR cameras along the Y-Axis independently along with the respective camera axis, both the modalities are positioned to image the side views of the breast 14, for example, the caudal, cranial, medial and lateral portion of the breast 14. Finally by actuating the rotational axis 8, the system is allowed to capture a full 360 degree view of the breast 14. The camera axis 5 is actuated/tilted to provide any desired tilt to the IR camera 12, 13 to capture a thermal image of the breast 14.

Ideally a common support system, the positioning assembly, supports both the infrared camera 12, 13 as well as X-ray system. When the Positioning assembly is actuated, it allows both the system, X-ray and Thermography to rotate simultaneously around a vertical axis relative to the hole or one at time as desired. The X-ray source 9 and the detector 11 are rotated in such a way that the patient's breast 14 on a portion of the patient's breast 14 always remains in the x-ray path 10.

Since the embodiments herein allows the X-ray source 9 to rotate around a vertical axis relative to the opening, the 360 degree view of the breast 14 is scanned in contradiction to the conventional mammography and thermography practices. Apart from this, the compression of the patient's breast 14 performed in a conventional mammography, is completely eliminated in the embodiments herein. Hence the system is more comfortable for the patients when compared to the existing systems. Within short time period, the patient's breast 14 is screened simultaneously in two modalities and the results are compared. The embodiments herein allows in case of biopsy is to be taken from the suspicious spot and/or a treatment is to be given using X ray radiation.

The microcontroller positions the Infrared imaging system and the X-ray imaging system to detect any abnormalities suspected. The microcontroller positions a biopsy device 15 to the suspected spot for a targeted biopsy procedure. The microcontroller positions the X-ray source 9 to expose a suspected spot to a targeted radiation for a post process treatment.

Figure 3:
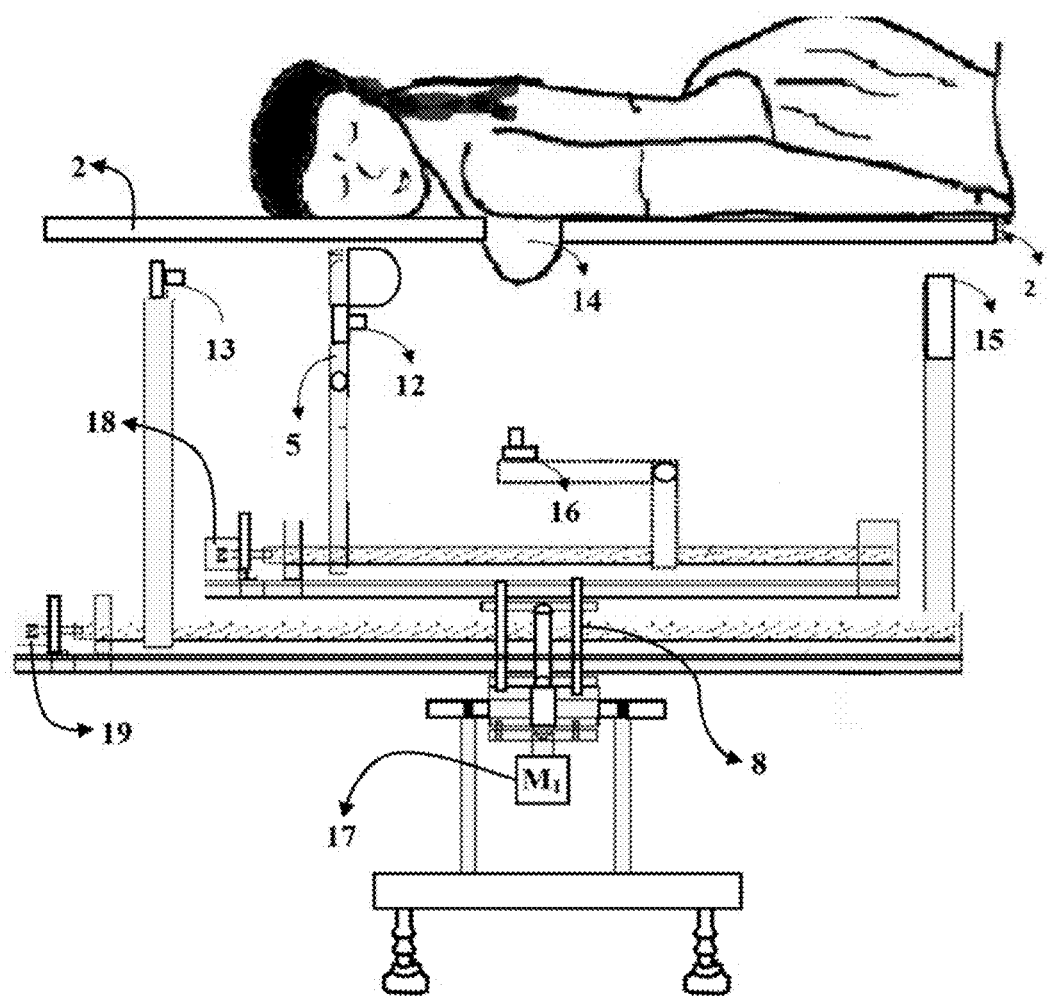
FIG. 3 illustrates a side view of the positioning assembly mounted with the Infra Red imaging system in an imaging device with a simultaneous digital X-Ray and Infrared red image acquisition and processing systems, according to an embodiment herein.

FIG. 3 illustrates a side view of the positioning assembly mounted with the Infra Red imaging system in an imaging device with a simultaneous digital X-Ray and Infrared red image acquisition and processing systems, according to an embodiment herein.

With respect to FIG. 3 represents the Thermography system. The positioning assembly is mounted with IR cameras 12, 13 to capture all the views which are not limited only to cranial, medial, caudal, lateral and frontal views of the breast 14. The IR imaging system is provided with two infrared cameras 12, 13, and actuated in such a way that one camera 12 is made to focus and image the portion of the breast which is under x-ray radiation and other camera 13 captures the other views of the breast under examination. Thus this arrangement reduces the procedural time.

The embodiments herein also enable the positioning of two infrared cameras 12, 13 in such a manner that one camera 12 is arranged in parallel to the X-ray source and another camera 13 is arranged in perpendicular to the x-ray source. The infrared camera 12 which is in parallel with the x-ray source captures the thermal images of the same portion of the breast 14 which is under x-ray radiation. As well as the camera 12 is used to study the impact of X-ray on the breast tissues (changes in heat pattern while breast is being subjected to X-ray). The position of X-ray source can be changed and can be positioned even very near to the breast for a better analysis. But in all the cases, the positioning assembly are positioned in such a way that both the X-ray source and infrared cameras 12, 13 do not come within the region of the breast opening provided in the table.

The positioning assembly comprises a microcontroller which will position to control the four axes such as the X-axis, Y-axis, Rotational axis and camera axis based on the commands from PC. Each axis is actuated by a separate motor 17, 18, 19 which is driven by the microcontroller. By actuating the X-Axis, the IR cameras 12, and the X-Ray source are moved along a horizontal axis. The IR camera 12 which is arranged in parallel to the X-ray source usually moves along the horizontal axis to capture a frontal shot of the breast 14. The IR camera 13 is actuated separately on X-axis for a biopsy procedure. By actuating the X-Axis, the IR cameras 12, 13 mounted on two different arms and the X-Ray source 9 are moved along a horizontal axis. The IR camera 12 which is arranged in parallel to the X-ray source 9 usually moves along the horizontal axis and the vertical axis to capture a frontal shot of the breast 14. The movement is limited by X-axis motor to avoid injury to the tissue being imaged. Similarly, by actuating the two IR cameras along the Y-Axis independently, along with the respective camera axis, both the modalities are positioned to image the side views of the breast 14, for example, the caudal, cranial, medial, frontal and lateral portion of the breast 14. Finally by actuating the rotational axis 8, the system is allowed to capture a full 360 degree view of the breast 14. The camera axis 5 is actuated/tilted to provide any desired tilt to the IR camera 12, 13 to capture a thermal image of the breast 14.

The microcontroller positions the Infrared imaging system and the X-ray imaging system to detect any abnormalities suspected. The microcontroller positions the X-ray source to expose a suspected spot to a targeted radiation for a post process treatment. The microcontroller positions a biopsy device 15 to the suspected spot for a targeted biopsy procedure.

During the clinical procedure, the patient is asked to lie down on the patient support 2 in prone position with one of their breast 14 being extended through the hole. The temperature controlled chamber is cooled to any desired temperature. Now the patient is ready for screening and once the patient is ready for screening, the user/technician selects either X-ray or Thermography or both for a screening process. For Thermography, the technician selects the views to be captured in a user interface provided in a PC. The user input is communicated to the microcontroller which in turn adjusts all the axes accordingly and images are automatically captured and loaded into the PC. In a similar way, the technician captures all the views of the breast and carries out a post processing analysis like 3D analysis.

For the X-ray system, the x-ray source starts sending a radiation beam which passes through the patient's breast 14 and captured by the detector. When the technician selects both the modes, both x-ray image and thermal image on the same region of the breast are captured simultaneously and loaded into the PC. These images are then displayed on the display screen separately and or overlapped to correlate the anatomical and physiological features of the breast under a scanned region.

When the technician selects both the modalities, the microcontroller actuates the motors to adjust the axes in such a way that both the systems scan the breast and rotate around the vertical axis in relative to the hole, so that a complete side view of the breast is screened in both the modalities simultaneously. While taking frontal image, the microcontroller disengages the x-ray system and moves the infrared camera 12 to position 16 in such a way that its focus is arranged to be parallel to the table top. Thus the embodiments herein are designed in such a way that two modalities do not interfere in other operative position.

The same procedure can be repeated for next breast also. The biggest and foremost advantage of the embodiments herein is that both the systems are positioned to the same co-ordinate exactly to focus the next breast at the specific/similar angle for a comparison with the images of the previous breast. For example, when an the abnormalities are found in a left breast at some angle, say A degree and at the co-ordinate X1,Y1 then the system is positioned exactly to the specific angle B (B=360-A degree) and same coordinate (X1,Y1) in the next breast also. So it will be very much useful to the radiologist to compare the results of normal Vs abnormal breast of same patient at a same/single visit.

Secondly, when any abnormality is suspected and marked for a follow-up procedure, then a duration of the follow-up procedure is very much reduced by this embodiments herein as the system of the embodiments herein is able to position both the modalities exactly to the suspected spot and facilitates targeted biopsy procedure. When the abnormality is diagnosed as a tumor, the embodiments herein are able to expose the tumor to a targeted radiation as a course of the treatment.

Figure 4:
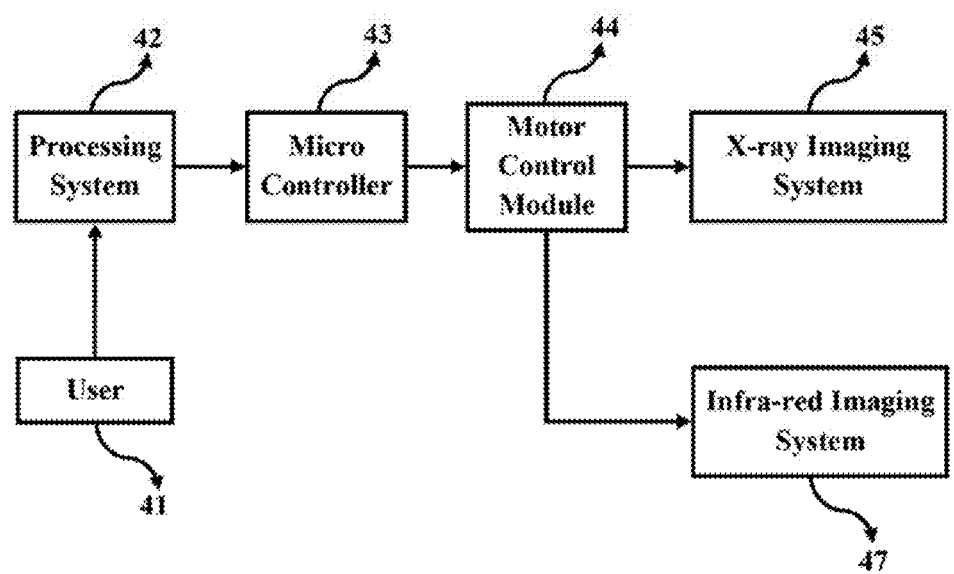
FIG. 4 illustrates a functional block diagram of a control system provided in a positioning assembly mounted with the X-RAY imaging system and the Infra Red imaging system in an imaging device with a simultaneous digital X-Ray and Infrared red image acquisition and processing systems, according to an embodiment herein.

FIG. 4 illustrates a functional block diagram of a control system provided in a positioning assembly mounted with the X-RAY imaging system and the Infra Red imaging system in an imaging device with a simultaneous digital X-Ray and Infrared red image acquisition and processing systems, according to an embodiment herein.

With respect to the FIG. 4, the positioning assembly has a microcontroller 43 to mote the X-ray source and detector in the X-ray imaging system 45 through a motor control module 44 and the plurality of infrared cameras in the infrared imaging system 47 through a respective motor along an x-axis and a y-axis, to rotate the X-ray source and the plurality of infrared cameras, and to tilt a camera axis of the plurality of infrared cameras based on a command provided by a user/technician 41 through a processing system 42 such as personal computer, and wherein the microcontroller 43 is communicatively connected to the processing system 42.

The microcontroller 43 positions the Infrared imaging system 47 and the X-ray imaging system 45 to detect any abnormalities suspected. The microcontroller 43 positions the X-ray source to expose a suspected spot to a targeted radiation for a post process treatment. The microcontroller 43 positions a biopsy device to the suspected spot for a targeted biopsy procedure.

During the clinical procedure, the patient is asked to lie down on the patient support in a prone position with one of their breast being extended through the hole. The temperature controlled chamber is cooled to any desired temperature. Now the patient is ready for screening and once the patient is ready for screening, the user/technician selects either X-ray or Thermography or both for a screening process. For Thermography, the technician 41 selects the views to be captured in a user interface provided in the processing system 42 such its a personal computer. The user input is communicated to the microcontroller 43 which in turn adjusts all the axes accordingly and images are automatically captured and loaded into the processing system 42. In a similar way, the technician captures all the views of the breast and carries out a post processing analysis like 3D analysis.

For the X-ray system, the X-ray source starts sending a radiation beam which passes through the patient's breast and captured by the detector. When the technician 41 selects both the modes, both the X-ray image and thermal image on the same region of the breast are captured simultaneously and loaded into the processing system 42, such as a personal computer. These images are then displayed on the display screen separately and or overlapped to correlate the anatomical and physiological features of the breast under a scanned region.

When the technician 41 selects both the modalities, the microcontroller 43 actuates the motor control modules 44 to control the motors to adjust the axes in such a way that both the systems 45, 47 scan the breast and rotate around the vertical axis in relative to the hole, so that a complete side view of the breast is screened in both the modalities simultaneously. While taking a frontal image, the microcontroller 43 disengages the X-ray imaging system 45 and moves the infrared camera alone in such a way that its focus is arranged to be parallel to the table. Thus the embodiments herein are designed in such a way that two modalities do not interfere in other operative position.

The same procedure can be repeated for next breast also. The biggest and foremost advantage of the embodiments herein is that both the systems 45, 47 are positioned to the same co-ordinate exactly to focus the next breast at the specific/similar angle for a comparison with the images of the previous breast. For example, when the abnormalities are found in a left breast at some angle, say A degree and at the co-ordinate X1,Y1, then the system is positioned exactly to the specific or similar angle B (B=360-A degree) and same coordinate (X1,Y1) in the next breast also. So, it will be very much useful to the radiologist to compare the results of normal Vs abnormal breast of same patient at a same/single visit.

Secondly, when any abnormality is suspected and marked for a follow-up procedure, then duration of the follow-up procedure is very much reduced by the system of the embodiments herein as the system of the embodiments herein is able to position both the modalities exactly to the suspected spot. When the abnormalities are diagnosed as a tumor, then the tumor is designed to be exposed to a targeted radiation as well as targeted biopsy.

The technical advantages of the embodiments herein includes providing a novel imaging device system with a simultaneous X-ray and Infrared image acquisition and processing system for an enhanced breast Imaging. The proposed device has a unique feature to capture the two different images in 360 degree of the breast tissue of the patient lying in a prone position by the integrated system.

The system of the embodiments herein helps in an accurate diagnosis by the outcome of two modalities taken simultaneously, thereby leading to a reduction in the number of false positive results when compared to the conventional techniques.

The system of the embodiments herein allows a capturing of a time based infra red images of the multiple views which include but not limited to the cranial, medial, caudal, lateral and frontal views of a breast.

The foregoing description of the specific embodiments herein will so fully reveal the general nature of the embodiments herein that others can, by applying current knowledge, readily modify and/or adapt for various applications such specific embodiments herein without departing from the generic concept, and, therefore, such adaptations and modifications should and are intended to be comprehended within the meaning and range of equivalents of the disclosed embodiments. It is to be understood that the phraseology or terminology employed in the embodiments herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art practice the embodiments herein with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A device with simultaneous X-ray and infrared acquisition and processing systems for an enhanced breast imaging to correlate anatomical and physiological characteristics of a breast and for a post processing of a 3D analysis, the device comprising:
    a positioning assembly;
    an X-ray imaging system mounted on the positioning assembly, wherein the X-ray imaging system comprises an X-ray source and an X-ray detector;
    an infrared imaging system mounted on the positioning assembly, wherein the infrared imaging system has a plurality of infrared cameras to acquire a plurality of infrared images of the breast to be examined, on a time basis, and wherein the plurality of infrared cameras includes a first infrared camera which is arranged in parallel to and in the same horizontal plane as the X-ray source, a second infrared camera which is arranged in perpendicular to and adjacent in the same vertical plane as the X-ray source and wherein the plurality of infrared images includes a cranial image, a medial image, a caudal image, a lateral image and a frontal image;
    a closed chamber housing the positioning assembly, infrared imaging system and the X-ray imaging system;
    a biopsy device;
    a patient support table to enable a patient to lie in a prone position; and an opening provided on the patient support table for extending a breast of a patient to be examined, through the patient table to acquire an image of the breast to be examined and
    wherein the positioning assembly is mounted with the infrared imaging system and the X-ray imaging system to capture an infra red image of the breast to be examined and an X-ray image of the breast to be examined simultaneously, and wherein the positioning assembly positions the infrared imaging system and the X-ray imaging system at a same coordinate point to acquire an image of both a right breast and a left breast of a patient at a specific or similar angle for comparison, and wherein a temperature and a humidity of the closed chamber is controlled and set as desired by a user, and wherein the X-Ray source is mounted so that a same portion of the breast is screened simultaneously by the X-ray imaging system and by the infrared imaging system to overlap a physiological characteristics of the breast with an anatomical characteristics of the breast to provide an enhanced analysis.

2. The device as claimed in claim 1, wherein the X-ray imaging system comprises the X-ray source to emit the X-ray radiation which passes through the breast to be examined and an X-ray detector for receiving the X-ray radiation which is passed through the breast to be examined to generate an X-ray image of the breast to be examined, and wherein the X-ray detector is placed close to a periphery of the breast to be examined.

3. The device as claimed in claim 1, wherein the first infrared camera focus a portion of the breast under an X-ray radiation and captures the cranial image, the medial image, the caudal image, the lateral image and the frontal image of the breast and wherein the second infrared camera captures the other portions of the breast at multiple views.

4. The device as claimed in claim 1, wherein the positioning assembly has a microcontroller to move the X-ray imaging system along X axis, rotational axis and camera axis and the plurality of infrared cameras along an x-axis and a y-axis, along with rotational and camera axis to rotate the X-ray source and the plurality of infrared cameras respectively based on a command provided by a user through a processing system, and wherein the processing system is a personal computer, and wherein the microcontroller is communicatively connected to the processing system.

5. The device as claimed in claim 4, wherein the microcontroller actuates a respective motor to move the X-ray source and the plurality of infrared cameras along the x-axis, the y-axis, a rotational axis and to tilt the camera axis of the plurality of infrared cameras.

6. The device as claimed in claim 1, wherein the Infrared imaging system and the X-ray imaging system are rotated simultaneously around a vertical axis in relative to the opening to acquire a full 360 degree view of the breast to be examined.

7. The device as claimed in claim 4, wherein the microcontroller positions the Infrared imaging system and the X-ray imaging system to detect any abnormalities suspected and wherein the microcontroller positions the X-ray source to expose a suspected spot with a targeted radiation for a post process treatment and wherein the microcontroller positions a biopsy device to the suspected spot for a targeted biopsy procedures.

8. The device as claimed in claim 1, wherein the Infrared imaging system and the X-ray imaging system are moved along a horizontal axis towards or away from the breast to be examined to perform an enhanced analysis.

9. The device as claimed in claim 1, wherein the Infrared imaging system and the X-ray imaging system are not allowed to be positioned within 20 cm from the edge of the opening in case of an imaging of side views and wherein the Infrared imaging system and the X-ray imaging system are not allowed to be positioned within 20 cm from the center of the opening in case of a frontal imaging at any instant so that no portion of the Infrared imaging system and the X-ray imaging system come into contact or touch the breast to be examined.

10. The device as claimed in claim 4, wherein the microcontroller tilt the plurality of infrared cameras to any required degree to screen a complete portion of the breast to be examined.

11. The device as claimed in claim 1, wherein a radiation impact of the X-Ray imaging system on a tissue of the breast is studied with the infrared images acquired from the Infrared imaging system.

12. The device as claimed in claim 1, wherein the infrared imaging system and the X-ray imaging system are used independently or simultaneously to cover a full portion of the breast for acquiring a desired image.

13. The device as claimed in claim 1, wherein the infrared imaging system and the X-ray imaging system are designed in such a way that a positioning of the infrared imaging system does not interfere with an operating position of the X-ray imaging system.

14. The device as claimed in claim 1, wherein the patient support table is configured to support the patient and exposes only the breast for screening and without making any discomfort to the patient.

15. The device as claimed in claim 1, wherein the patient support table and the closed chamber are coated with Lead (Pb) to avoid a leakage of an X-Ray radiation.

* * * * *